United States Patent [19]

Rokos

[11] Patent Number: 5,621,528
[45] Date of Patent: Apr. 15, 1997

[54] METHOD AND DICHROGRAPH FOR MEASUREMENT OF CIRCULAR DICHROISM, OPTICAL ROTATION AND ABSORPTION SPECTRA

[75] Inventor: Jiri Rokos, Prague, Czech Rep.

[73] Assignee: Rokos & Co., Ltd., Prerov, Czechoslovakia

[21] Appl. No.: 495,468

[22] PCT Filed: Nov. 25, 1994

[86] PCT No.: PCT/CZ94/00026

§ 371 Date: Jul. 26, 1995

§ 102(e) Date: Jul. 26, 1995

[87] PCT Pub. No.: WO95/14919

PCT Pub. Date: Jun. 1, 1995

[30] Foreign Application Priority Data

Nov. 26, 1993 [CZ] Czech Rep. ............... 2566-93

[51] Int. Cl.[6] ................................................ G01J 4/00
[52] U.S. Cl. .................. 356/364; 356/368; 356/366; 356/327
[58] Field of Search .................. 356/364–369, 356/370, 319, 432–442, 326, 322, 327; 250/225; 128/633–634, 664–665

[56] References Cited

U.S. PATENT DOCUMENTS

| | | | |
|---|---|---|---|
| 3,345,907 | 10/1967 | Akiyoshi Wada | 356/367 |
| 3,741,660 | 6/1973 | Abu-Shumays et al. | 356/366 |
| 3,831,436 | 8/1974 | Sanford | 356/364 |
| 4,309,110 | 1/1982 | Tumerman | 356/366 |
| 4,589,776 | 5/1986 | Carver et al. | 356/367 |
| 4,725,140 | 2/1988 | Musha | 356/364 |
| 4,799,796 | 1/1989 | Musha | 356/364 |
| 5,036,204 | 7/1991 | Leyden | 356/364 |
| 5,298,973 | 3/1994 | Fukagaroa et al. | 356/368 |

OTHER PUBLICATIONS

Journal Of Physics E; Scientific Instruments, vol. 7, No. 12, Dec. 1974, pp. 991–996.
Review of Scientific Instruments, vol. 61, No. 8, 1990, pp. 2073–2079.
Journal of Physics D. Applied Physics, vol. 24, No. 7, pp. 1187–1192.

*Primary Examiner*—Hoa Q. Pham
*Attorney, Agent, or Firm*—Jacobson, Price, Holman & Stern, PLLC

[57] ABSTRACT

The dichrograph and accompanying method are usable for parallel measurement of circular dichroism according to the first harmonic of photoelectric current of the detector, optical rotation according to the second harmonic and transparency according to the null harmonic. It contains the switch (3) of ray, from which alternatively exit two parallel rays—measurement ray (4) and reference ray (5), going through one mutual modulator of ellipticity (6), achromatic phase element (9) which is during calibration of circular unit situated in the reference ray (5). Moreover it contains two analyzers—the measurement analyzer (8) in the measurement ray (4) behind the couvette (7) and the reference analyzer (10) in the reference ray (5). The measurement analyzer (8) has the optical axis turned for 45° same as the modulator (6). The reference analyzer (10) is during measurement turned for unit angle, e.g. for 1°, to the measurement analyzer (8).

7 Claims, 2 Drawing Sheets

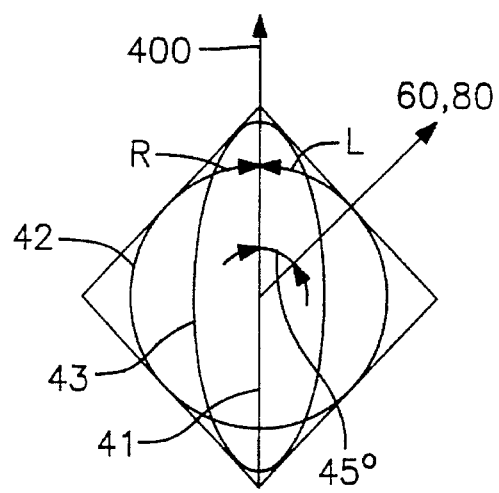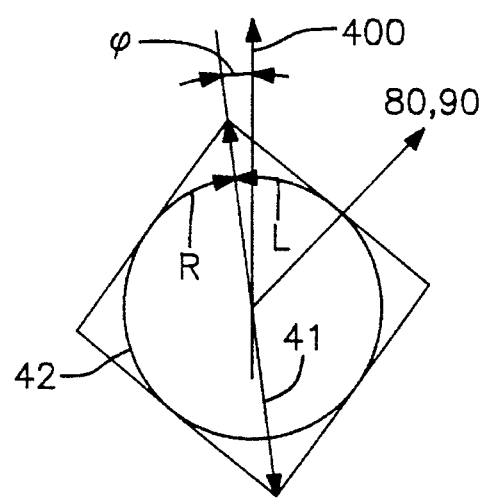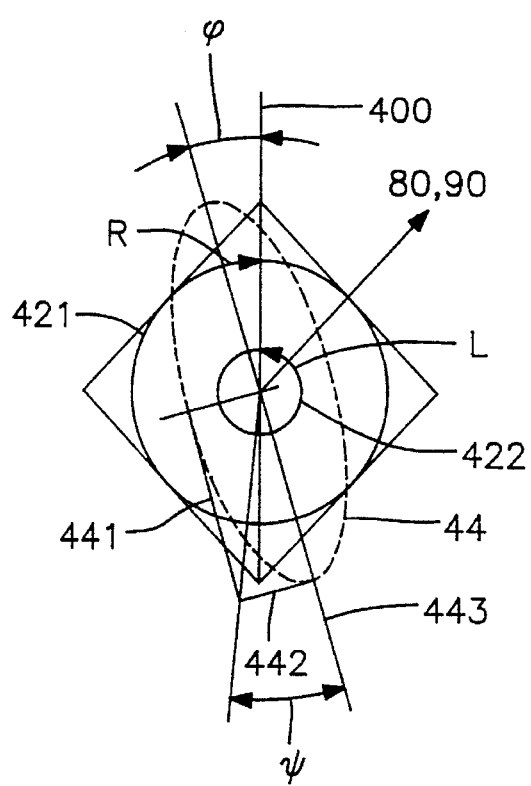

METHOD AND DICHROGRAPH FOR MEASUREMENT OF CIRCULAR DICHROISM, OPTICAL ROTATION AND ABSORPTION SPECTRA

BACKGROUND OF THE INVENTION

Subject of this invention is the method for measurement of circular dichroism, optical rotation and absorption on spectra on optical active, gyrotropic, substances by way of spectropolarization and construction of an apparatus for performance of this measurement.

Presently circular dichroism spectra can be measured by spectropolarimetric apparatus, dichrographs, which after refitting of its optical system can be used for measurement of other optical properties such as optical rotation and/or absorption on a tested substance as well. For measurement of circular dichroism the apparatus has to contain at least a light source of known wavelength, linear polarizer, modulator of ellipticity, holder and/or couvette for tested substance and detector. For measurement of optical rotation by the same apparatus it is necessary to install before the detector an analyzer which transfers the polarization plane into a change in the ray amplitude. For measurement of absorption, it is advantageous to eliminate, from the optical system, polarization elements i.e. polarizer, ellipticity modulator and analyzer.

Practically it means that by presently used methods with utilization of known types of dichrographs all three above mentioned optical properties cannot be measured simultaneously i.e. in real time. It is not convenient mainly in cases when properties or compositions of tested substances are changing quickly during the chemical reaction or in the cases when non-stable organic substances as e.g. hyaluronidase are measured.

The other imperfection of present dichrographs is in fact that they do not enable utilization of a reference ray for determination of a corresponding unit of the circular dichroism, because in practice there are not available etalon substances showing constant circular dichroism in an acceptably wide spectral area for example in an interval from 300 to 600 nm. This fact limits precision of measurements preformed on presently known dichrographs.

The goal of the invention is to improve the measurement method which substantially reduces the above-mentioned disadvantages and enables, after modification of presently known dichrographs, simultaneous measurement of circular dichroism, optical rotation and absorption spectra in real time and an acceptably wide spectral interval.

SUMMARY OF THE INVENTION

The above mentioned goal is achieved by the subject of this invention, which is a method for measurement of transmittance, circular dichroism and optical rotation of an optical active substance, during which is for determined wavelength, after previous calibration of the measurement system and determination of unit values ascertained by means of harmonic analysis of the state of polarization of a measurement ray with modulated ellipticity after passing through the optically active substance and analyzer where the changes of the measured ray amplitude are transferred into changes in electric signals.

An object of the method according to this invention is to assort the null harmonic, the first harmonic and the second harmonic component which correspond to transmittance, circular dichroism and optical rotation of measured optically active substance, while the frequency of the first harmonic component corresponds to modulation frequency, and the amplitudes of the such determined harmonic components are compared with individual unit values achieved by calibration.

A further object of the method according to this invention is to utilize double ray equipment which forms the second ray as a reference ray such that the reference ray is calibrated and modulated identically with the measurement ray and changes in the amplitude of the reference ray are transformed into changes in the electric signal changes alternatively with transferring of corresponding changes of measurement ray amplitudes, wherein the frequency of alternations of both the rays, the measurement ray and the reference ray, is at least 10× smaller than the modulation frequency.

A dichrograph is provided for carrying out this method, formed by the source of ray of known wavelength, linear polarizer, modulator of ellipticity, connected with the generator of modular voltage, measured sample, analyzer and detector of electromagnetic radiation, the output of which is connected to at least two short range amplifiers. Behind the linear polarizer in the inlet ray, there is a direction switch for the ray behind which are formed two rays, a measurement ray and a reference ray. Further, in the path of the measurement ray is an ellipticity modulator of the measurement ray connected to the generator of modulation voltage and a measurement analyzer, wherein the optical axes of measurement analyzer is with regard to the optical axis of the linear polarizer oriented under the angle 45°, and between them is placed the measured sample, for example couvette, and wherein, in the path of the reference ray, there is a further ellipticity modulator for the reference ray, which optical axis is with regard to the optical axis of the linear polarizer oriented under the angle 45° and in the path of the mentioned reference ray is further placed at least a reference analyzer, which optical axis is to the optical axis of the linear polarizer oriented under the angle 45°± unit angle $\alpha$. In the paths of the measurement ray and reference ray are further situated optical elements, advantageously mirrors for directing of those rays on the mutual detector of electromagnetic radiation, the outputs of which are connected to a triad of short range amplifiers, AC amplifier, the first short range amplifier with a working frequency corresponding to the frequency of the ellipticity modulators and the second short range amplifier, which has a working frequency corresponding to double the frequency of the ellipticity modulators. Further in the paths of the measurement ray and reference ray, there is a ray interrupter situated. The unit angle advantageously has a value ±0.1° to ±40°.

Moreover the ray interrupter may form a part of the switch of the inlet ray, and the ellipticity modulator of the measurement ray and the ellipticity modulator of the reference ray may be formed as a mutual ellipticity modulator.

Finally, according to this invention, the source of inlet ray may be formed by a monochromator.

The measurement method and dichrograph which are subject of this invention provide, against the present stage of techniques, substantial progress in the possibility of measuring simultaneously, in real time, all three of the above mentioned optical characteristics, i.e. circular dichroism, optical rotation and absorption or to test which optical properties can be measured on actual tested substances. Another advantage of the subject of this invention is that possibility to arrange continual measurement in wide wavelength scale.

BRIEF DESCRIPTION OF THE DRAWINGS

Examples of dichrograph arrangements are schematically shown on the enclosed drawings.

FIGS. 2–4 show stages of polarized rays in planes A and B according to FIG. 1.

DESCRIPTION OF THE PREFERRED EMBODIMENT

Figure 1:
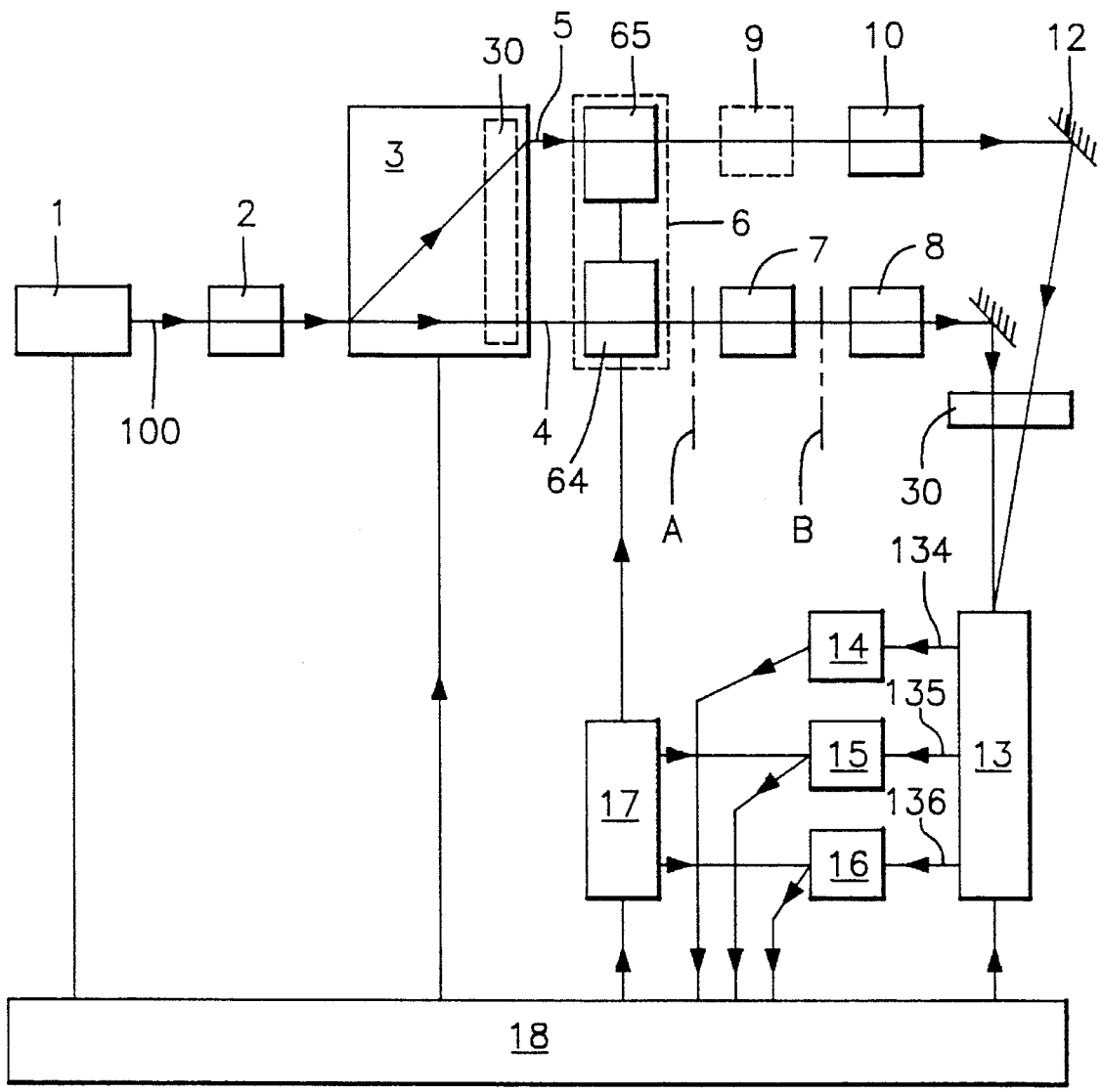
FIG. 1 shows a layout of the dichrograph.

The dichrograph according to FIG. 1 is formed by the source 1 of inlet monochromatic ray 100, e.g. laser or monochromatic rays with adjustable wavelength—for example a monochromator. The inlet ray 100 goes through linear polarizer 2 and enters the ray switch 3 formed by, for example, a combination semitransmittable and reflectable mirror. Behind the ray switch 3 the ray 100 is situated in an interrupter 30 formed, for example, by an electronically controlled rotation element-chopper. From the interrupter 30 the outlet ray emanates alternatively as measurement ray 4 or reference ray 5. The alternation is performed using a preadjusted switching frequency.

The measurement ray 4 goes further through a modulator 64 for modulating the measurement ray ellipticity, measured sample 7, e.g. couvette with the solution, the parameters of which are to be measured, measurement analyzer 8, which is formed by for example a crystal polarizer of common construction and mirror 11 to a detector 13 which can be some sensor of electromagnetic radiation, for example, some convenient photoelectric sensor such as a photoelectric multiplier.

The reference ray 5 goes through the reference modulator 65 for modulating the ellipticity, which modulator 65 is the same as the measurement modulator 64 of the measurement ray. Advantageously, both modulators can be realized as a mutual modulator 6. Then the reference ray 5 goes through achromatic quarterwave phase element 9 which can be formed by a couple of mutually counter-oriented plates made from anizotrop material. One of those plates is radially movable and is brought into the reference ray 5 alternatively as mentioned further. The reference ray 5 goes further through the reference analyzer 10, which has the same elements and parameters as the measurement analyzer 8. After exiting from the reference analyzer, the reference ray 5 is directed in the same direction as the measurement ray 4, by means of the mirror 12 toward the same detector 13 of the electromagnetic radiation.

Connected to the outputs 134, 135 and 136 of detector 13 are triad amplifiers, AC amplifier 14, the first short range amplifier 15 and the second short range amplifier 16. Short range amplifiers 15 and 16 are formed for example as synchronous detectors in common connection and are connected with generator 17 of alternate voltage from which one voltage of lower frequency is used for control of modulator 64 and 65 for modulation of ellipticity of the measurement and reference ray or control of mutual modulator 6. The second voltage has double the frequency and is used for the second short range amplifier 16. One necessary condition for proper operation of the dichrograph constructed according to this invention is that the working frequency of generator 17 is substantially, at least 10 times larger, than the working frequency of the ray interrupter 30 i.e. frequency at which the inlet ray 100 is switched between the direction of the measurement ray 4 and that of the reference ray 5. During operation of the invention according to FIG. 1, the working frequency of the interrupter 30 of rays is for example 100 Hz, while the working frequency of the generator 17 of modulation voltage is 50 kHz.

The whole system of dichrograph according to FIG. 1 is completed by control, registration and evaluation equipment 18 which are not bound on the subject of this invention and can consist of the control computer equipped with necessary software.

On FIG. 2 are screened, to the plane of the drawing, space stages of polarization of the inlet ray 100 in the plane A according to the FIG. 1—i.e. in front of the measured sample 7. Corresponding electric vector 41 is transferred during modulation into the form of an ellipse, ring and vice versa. The linearly polarized state corresponds to the state of polarization under zero voltage on the modulator 64 of the measurement ray or on modulator 65 of the reference ray 5.

FIG. 3 shows the position of electric vector 41 of linearly polarized inlet ray 40 in the plane B according to FIG. 1 i.e. after its passing through the couvette 7 with the measured sample in the case that this shows the optical rotation only. FIG. 4 shows positions and/or states of the electric vector 41 in the case that the measured sample shows circular dichroism only. It is seen from FIG. 4 that amplitudes of the left turning component 421 and right turning component 422 are due to different physical properties of the measured substance. As a result of this fact, their interference on the outlet from the measured sample 7 causes the end of the corresponding resulting electric vector to form the ellipse, which is marked by the dashed line in FIG. 4. In the case that the measured sample 7 shows as good an optical rotation as circular dichroism the axis of the resulting ellipse is turned for a certain angle $\phi$ and ellipticity is determined by the angle $\psi$, the tangent of which is determined by the ratio of the small half axis 442 and large half axis 441 as is seen on FIG. 4. Due to the fact that the measured sample 7 practically always shows some absorption, the amplitude of the corresponding vector on the plane B according to FIG. 1, i.e. behind the measured sample 7 is smaller than the corresponding amplitude of the same vector on the plane A i.e. before the measured sample 7.

Measurement of optical parameter values is based on a comparison between the state of measurement ray 4 before the measurement analyzer 8 and the reference ray 5 before the reference analyzer 10 according to FIG. 1.

The measurement ray 4 is for example after passing by modulator 64 of the measurement ray 4, ellipticity modulated as shown on FIG. 2. In the case that the measured sample 7 shows all three measured parameters i.e. some absorption, circular dichroism and optical rotation, amplitudes as well as corresponding intensities of the ray electric components are changing proportionally to values of measured parameters. Those changes are related to the original plane 400 of the linearly polarized measurement ray and corresponding angle position of the measurement analyzer 8.

In the second wing, the reference ray 5 is polarized on the outlet from the modulator 65 of the reference ray 5 in the same manner as the measurement ray 4 at the output from the modulator 64. The reference analyzer 10 is according to this invention oriented so that its polarization plane is with regard to corresponding polarization plane of measurement analyzer 8 turned for a certain preselected and adjusted unit angle $\alpha$, for example 1°. After passing of the reference ray 5 through reference analyzer 10 intensities I of the measurement ray 4 and reference ray 5 are changed so that on outputs 134, 135, 136 of detector 13 electric currents are generated which contain zero harmonic components proportionate to the absorption associated with the measured substance, the first harmonic component proportionate to the value of circular dichroism of the measured substance and the second harmonic component proportionate to optical rotation of the measured substance. Individual measured components are related to the basic harmonic which corresponds to the generator 17 frequency of modulation voltage of modulator 64 and 65 for the measuring and reference rays. For amplitudes of individual specified harmonic components, the following reactions are valid:

for the null harmonic $$I_0 = k_0 \times \tau$$

for the first harmonic $$I_1 = k_1 \times \sin \psi$$

for the second harmonic $$I_2 = k_2 \times \sin \phi$$

where :

$\tau$=transmissivity coefficient of the measured substance $$\psi = 1/2 \arcsin \frac{\tau_R - \tau_L}{\tau_R + \tau_L}$$

$$\phi = 1/2 (\delta_R - \delta_L)$$

$\tau_R$, $\tau_L$—transmittance coefficients of circularly polarized rays R and L $\delta_R$, $\delta_L$—phase shifting of rays R and L $\psi$—ellipticity caused by circular dichroism $\phi$—turning of the polarization plane caused by the optical rotation Coefficients $k_0$, $k_1$ and $k_2$ are determined as constants of a measurement system by calibration before the measurement as follows:

Coefficient $k_0$ is determined by the difference in photoelectric currents in cases when the measured sample 7 is formed by the couvette according to FIG. 1 when filled with a substance with transmittance $\tau=1$, e.g. distilled water and then is filled by a substance with transmittance $\tau=0$, which can be simulated by closing of measurement ray 4.

For measurement of coefficient $k_1$, an achromatic quarterwave phase element 9 is installed into the measurement ray 4, before the measurement analyzer 8. The achromatic quarterwave phase element, 9 is oriented under the angle 45° with reference to the plane of electric vector 40 which together with the measurement analyzer 8 oriented with reference to the plane of the electric vector 40 under the angle 45°+α simulates the presence of etalon achromatic dichroic substance, which causes ellipticity of the measurement ray 4 of value $\psi=\alpha$. The value $\psi$ is independent of the wavelength of source 1 of inlet ray 100. The value $k_1$ is determined from the difference in values of photoelectric currents under orientation of the measurement analyzer 8 either under the angle 45°, or after its following turning for selected unit angle e.g. 1°. In practice, it is advantageous to select the unit angle from the interval ±0.1° to ±40°. In a similar manner, the coefficient $k_2$ is determined after elimination of the achromatic quarterwave phase element 9.

In the same manner, it is possible to measure proportionality coefficients $k_0$, $k_1$ and $k_2$ corresponding to the reference ray 5. All coefficients of proportionally are registered in the evaluation equipment 18. During the measurement of a few wavelengths for example with the monochromator as the source 1 of inlet monochromatic ray 100, coefficients $k_0$, $k_1$ and $k_2$ are determined analogously for all demanded wavelengths.

After completing calibration, which is done after the first installation and/or for periodic testing measurements, the achromatic quarterwave phase element 9 is eliminated from the optical path and the reference analyzer 10 remains turned for the mentioned unit angle. The measurement analyzer 8 is turned into the original position α=0°.

During the measurement of the sample 7, are due to the interrupter 30 of the ray compared amplitudes of null harmonic measurement, and reference rays what enables to achieve the transmittance coefficient τ of measured sample 7 and in the same time amplitudes of the first and second harmonic corresponding to the measurement ray 4, are compared with the unit amplitudes of the second harmonic which corresponds to the reference ray 5, what enables to receive values of circular dichroism and optical rotation. Ratio of the first and second harmonic of the reference ray 5 was obtained during calibration and is memorized and registered during calibration by the evaluation equipment 18.

Utilization of the reference ray 5 which is advantageously modulated, for example, by common modulator 6 in the same way as the measurement ray 4 enables one to achieve high reproducibility in the measurement of absorption, circular dichroism and optical rotation due to elimination of fluctuation of the source 1, mutual modulator 6, ellipticity sensitivity of detector 13 and, by this, fluctuation of the whole connected electronic chain. The stability of mutual modulator 6 is moreover during measurement continually assured by continual check up of reference ray 5 ratio of null and second harmonic amplitudes.

The high precision of measurement is provided by the precision of micrometric screws for turning of the measurement analyzer 8 and reference analyzer 10. Increase of circular dichroism measurement precision is achieved by simulation of an achromatic unit etalon by combination of the achromatic quarterwave phase element 9 and the reference analyzer 10 which can be under presence of achromatic quarterwave phase element 9 utilized as a compensator of circular dichroism. In this case the dichrograph enables measurements with the maximum precision by means of a null compensation method.

The method for measurement of spectropolarimetric characteristics of optically active substances and the dichrograph according to this invention can be, thanks to the possibility of having immediately available values of absorption, optical rotation and circular dichroism and to the possibility of realizing measurement for wavelengths selected from the determined spectral range, successfully utilized for research of gyrotropic substances namely from the area of organic chemistry pharmacology, biophysics, biochemistry etc.

I claim:

1. A method for measuring transmittance, circular dichroism and optical rotation of an optical active substance, for a predetermined wavelength, comprising the steps of:

calibrating a measurement system which produces a measurement ray, by performing harmonic analysis of a polarization state of said measurement ray to determine unit values;

performing ellipticity modulation on the measurement ray to create an ellipticity modulated ray;

directing the ellipticity modulated ray through said optical active substance and into an analyzer;

transforming changes in amplitude of said ellipticity modulated ray into changes in electrical signals at said analyzer;

assorting a null harmonic component, a first harmonic component, and a second harmonic component to respectively correspond to transmittance, circular dichroism and optical rotation of the optical active substance, wherein a frequency of said first harmonic component corresponds to a modulation frequency; and comparing amplitudes of said null, first and second harmonic components to said unit values.

2. The method of claim 1, and further comprising the steps of:

forming a reference ray distinct from said measurement ray;

calibrating said reference ray and elliptically modulating said reference ray in the same manner that the measurement ray is calibrated and elliptically modulated to thereby create an ellipticity modulated reference ray;

transforming changes in amplitude of said elliptically modulated reference ray into changes in said electrical signals, alternatingly with said step of transforming changes in amplitude of said ellipticity modulated ray into changes in said electrical signals, said steps of transforming being carried out with alternations at an alternation frequency which is at least ten times smaller than the modulation frequency.

3. A dichrograph for measuring transmittance, circular dichroism and optical rotation of an optical active substance, for a predetermined wavelength, said dichrograph comprising:

a light source capable of producing a ray of light having said predetermined wavelength;

a linear polarizer arranged for placement in a path of said ray of light;

a ray switch for splitting said ray of light into a measurement ray and a reference ray;

a ray interruptor located in the path of said measurement ray and in the path of said reference ray, for interrupting said measurement ray and reference ray;

at least one ellipticity modulator responsive to a modulation voltage, for modulating an ellipticity of said measurement ray and for modulating an ellipticity of said reference ray in accordance with said modulation voltage, to generate an ellipticity modulated measurement ray and an ellipticity modulated reference ray;

a measurement ray analyzer disposed in the path of said ellipticity modulated measurement ray, said measurement ray analyzer having an optical axis oriented at an angle of less than 45 degrees with respect to an optical axis of said linear polarizer, said measurement ray analyzer and said at least one ellipticity modulator being sufficiently spaced apart from one another that said optical active substance can be accommodated therebetween;

a reference ray analyzer disposed in the path of said ellipticity modulated reference ray, said reference ray analyzer having an optical axis oriented at an angle of less than 45 degrees ± a unit angle ($\alpha$) with respect to said optical axis of said linear polarizer;

a mutual detector of electromagnetic radiation responsive to said ellipticity modulated reference ray and ellipticity modulated measurement ray so as to produce electrical output signals;

an AC amplifier electrically connected to a first of said electrical output signals;

a first short range amplifier electrically connected to a second of said electrical output signals, said first short range amplifier having a working frequency corresponding to a frequency of said at least one ellipticity modulator; and a second short range amplifier electrically connected to a third of said electrical output signals, said second short range amplifier having a working frequency which is double said frequency of said at least one ellipticity modulator; and at least one optical element for directing at least one of said ellipticity modulated reference ray and ellipticity modulated measurement ray toward said mutual detector of electromagnetic radiation.

4. The dichrograph according to claim 3, wherein said unit angle ($\alpha$) has a value of ±0.1 degrees to ±40 degrees.

5. The dichrograph according to claim 3, wherein said ray interruptor is part of said ray switch.

6. The dichrograph according to claim 3, wherein said at least one ellipticity modulator comprises a single mutual ellipticity modulator for modulating an ellipticity of said measurement ray and of said reference ray.

7. The dichrograph according to claim 3, wherein said source comprises a monochromator.

* * * * *